(12) United States Patent
Dobrinsky

(10) Patent No.: US 11,173,221 B2
(45) Date of Patent: Nov. 16, 2021

(54) ULTRAVIOLET DISINFECTION FOR A WATER BOTTLE

(71) Applicant: Sensor Electronic Technology, Inc., Columbia, SC (US)

(72) Inventor: Alexander Dobrinsky, Silver Spring, MD (US)

(73) Assignee: Sensor Electronic Technology, Inc., Columbia, SC (US)

( * ) Notice: Subject to any disclaimer, the term of this patent is extended or adjusted under 35 U.S.C. 154(b) by 0 days.

(21) Appl. No.: 16/176,336

(22) Filed: Oct. 31, 2018

(65) Prior Publication Data

US 2019/0125907 A1 May 2, 2019

Related U.S. Application Data

(60) Provisional application No. 62/579,876, filed on Oct. 31, 2017.

(51) Int. Cl.
| | |
|---|---|
| *A61L 2/10* | (2006.01) |
| *B08B 7/00* | (2006.01) |
| *A47G 19/22* | (2006.01) |
| *B65D 51/24* | (2006.01) |
| *B65D 47/24* | (2006.01) |
| *B65D 47/14* | (2006.01) |
| *A45F 3/16* | (2006.01) |

(52) U.S. Cl.
CPC ................ *A61L 2/10* (2013.01); *A45F 3/16* (2013.01); *A47G 19/2266* (2013.01); *A47G 19/2272* (2013.01); *B65D 47/147* (2013.01); *B65D 47/243* (2013.01); *B65D 51/24* (2013.01); *A45F 2003/163* (2013.01); *A47G 2400/02* (2013.01); *B08B 7/0057* (2013.01); *C02F 2307/02* (2013.01)

(58) Field of Classification Search
None
See application file for complete search history.

(56) References Cited

U.S. PATENT DOCUMENTS 5,292,021 A * 3/1994 Lyon .................. A47G 23/0258
220/253
5,919,365 A * 7/1999 Collette .................... A45F 3/20
210/419

(Continued)

FOREIGN PATENT DOCUMENTS

WO WO-2017185217 A1 * 11/2017 ............. B65D 51/24

*Primary Examiner* — Michael J Logie
(74) *Attorney, Agent, or Firm* — LaBatt, LLC

(57) ABSTRACT

Disinfection of a surface, such as a mouthpiece of a water bottle, using ultraviolet radiation is disclosed. A cover assembly can include a cover configured to selectively enclose the surface to be disinfected, such as the mouthpiece. The cover assembly can be configured such that ultraviolet radiation can be emitted into an interior volume at least partially formed by the cover and including the surface. The cover assembly can further include a power source which provides power to one or more ultraviolet light sources that emit the ultraviolet radiation. The cover assembly can be a mouthpiece cover assembly physically separate from a container and top cover or integrated in the top cover. A container and a top cover including one or more features for improved cleanliness are also disclosed.

20 Claims, 3 Drawing Sheets

(56) References Cited

U.S. PATENT DOCUMENTS

| | | | |
|---|---|---|---|
| 6,004,460 A * | 12/1999 | Palmer | C02F 1/003 210/209 |
| 6,565,743 B1 * | 5/2003 | Poirier | B65D 51/00 116/284 |
| 7,537,141 B1 * | 5/2009 | Robinson | B65D 47/147 222/543 |
| 7,553,456 B2 | 6/2009 | Gaska et al. | |
| 7,634,996 B2 | 12/2009 | Gaska et al. | |
| 8,277,734 B2 | 10/2012 | Kuodymov et al. | |
| 8,975,596 B1 * | 3/2015 | Matthews | C02F 1/325 250/432 R |
| 8,980,178 B2 | 3/2015 | Gaska et al. | |
| 9,006,680 B2 | 4/2015 | Bettles et al. | |
| 9,034,271 B2 | 5/2015 | Shur et al. | |
| 9,061,082 B2 | 6/2015 | Gaska et al. | |
| 9,138,499 B2 | 9/2015 | Bettles et al. | |
| 9,179,703 B2 | 11/2015 | Shur et al. | |
| 9,572,903 B2 | 2/2017 | Dobrinsky et al. | |
| 9,603,960 B2 | 3/2017 | Dobrinsky et al. | |
| 9,687,577 B2 | 6/2017 | Dobrinsky et al. | |
| 9,707,307 B2 | 7/2017 | Shur et al. | |
| 9,718,706 B2 | 8/2017 | Smetona et al. | |
| 9,724,441 B2 | 8/2017 | Shur et al. | |
| 9,750,830 B2 | 9/2017 | Shur et al. | |
| 9,757,486 B2 | 9/2017 | Dobrinsky et al. | |
| 9,795,699 B2 | 10/2017 | Shur et al. | |
| 9,801,965 B2 | 10/2017 | Bettles et al. | |
| 9,802,840 B2 | 10/2017 | Shturm et al. | |
| 9,878,061 B2 | 1/2018 | Shur et al. | |
| 9,919,068 B2 | 3/2018 | Shur et al. | |
| 9,974,877 B2 | 5/2018 | Bettles et al. | |
| 9,981,051 B2 | 5/2018 | SHur et al. | |
| 9,987,383 B2 | 6/2018 | Bilenko et al. | |
| 9,999,782 B2 | 6/2018 | Shur et al. | |
| 10,004,821 B2 | 7/2018 | Dobrinsky et al. | |
| 10,040,699 B2 | 8/2018 | Smetona et al. | |
| 10,099,944 B2 | 10/2018 | Smetona et al. | |
| 2006/0165571 A1 * | 7/2006 | Seon | A61J 11/008 422/302 |
| 2008/0203005 A1 * | 8/2008 | Francisco | B01D 61/18 210/238 |
| 2011/0278206 A1 * | 11/2011 | Hull | C02F 1/003 210/85 |
| 2013/0048545 A1 | 2/2013 | Shatalov et al. | |
| 2013/0214007 A1 * | 8/2013 | Simonian | B65D 51/1644 222/189.06 |
| 2013/0319915 A1 * | 12/2013 | Gellibolian | C02F 1/002 210/87 |
| 2014/0202948 A1 * | 7/2014 | Li | C02F 1/008 210/251 |
| 2014/0202962 A1 | 7/2014 | Bilenko et al. | |
| 2015/0053624 A1 * | 2/2015 | Maiden | C02F 1/325 210/748.11 |
| 2015/0217011 A1 * | 8/2015 | Bettles | A61L 2/10 250/435 |
| 2016/0031720 A1 * | 2/2016 | May | C02F 1/003 210/244 |
| 2016/0107904 A1 * | 4/2016 | Rajagopalan | C02F 1/325 250/432 R |
| 2016/0114067 A1 * | 4/2016 | Dobrinsky | G01N 21/6486 250/461.1 |
| 2016/0114186 A1 | 4/2016 | Dobrinsky et al. | |
| 2016/0166094 A1 * | 6/2016 | Tebbe | A47G 19/2272 220/709 |
| 2016/0355412 A1 * | 12/2016 | Collins | C02F 1/325 |
| 2017/0057841 A1 * | 3/2017 | Blood | C02F 1/325 |
| 2017/0057842 A1 | 3/2017 | Dobrinsky et al. | |
| 2017/0100495 A1 | 4/2017 | Shur et al. | |
| 2017/0189711 A1 | 7/2017 | Shur et al. | |
| 2017/0245527 A1 | 8/2017 | Dobrinsky et al. | |
| 2017/0245616 A1 | 8/2017 | Lakios et al. | |
| 2017/0280737 A1 * | 10/2017 | Liao | A23L 3/28 |
| 2017/0281812 A1 | 10/2017 | Dobrinsky et al. | |
| 2017/0290934 A1 | 10/2017 | Dobrinsky et al. | |
| 2017/0368215 A1 | 12/2017 | Shatalov et al. | |
| 2018/0028700 A1 | 2/2018 | Dobrinsky et al. | |
| 2018/0092308 A1 | 4/2018 | Barber et al. | |
| 2018/0104368 A1 | 4/2018 | Dobrinsky et al. | |
| 2018/0117194 A1 | 5/2018 | Dobrinsky et al. | |
| 2018/0185529 A1 | 7/2018 | Shur et al. | |
| 2018/0194645 A1 * | 7/2018 | Hsu | C02F 1/32 |
| 2018/0221521 A1 | 8/2018 | Shur et al. | |
| 2018/0243458 A1 | 8/2018 | Shatalov et al. | |
| 2018/0339075 A1 | 11/2018 | Kennedy et al. | |
| 2019/0030477 A1 | 1/2019 | Shatalov | |
| 2019/0038008 A1 * | 2/2019 | Lee | A45F 3/18 |
| 2019/0090998 A1 * | 3/2019 | Ertl | A61C 5/50 |
| 2019/0099613 A1 | 4/2019 | Estes et al. | |
| 2019/0100445 A1 | 4/2019 | Dobrinsky et al. | |
| 2019/0100718 A1 | 4/2019 | Estes et al. | |
| 2019/0117811 A1 | 4/2019 | Barber, III | |

* cited by examiner

ULTRAVIOLET DISINFECTION FOR A WATER BOTTLE

REFERENCE TO RELATED APPLICATIONS

The current application claims the benefit of U.S. Provisional Application No. 62/579,876, filed on 31 Oct. 2017, which is hereby incorporated by reference.

TECHNICAL FIELD

The disclosure relates generally to water bottles, and more particularly, to a solution for disinfecting a surface of and/or fluid within the water bottle using ultraviolet light.

BACKGROUND ART

Reusable water bottles have become a ubiquitous part of people's lives. Effectively cleaning a water bottle between uses is important. However, such cleaning can be difficult to achieve for some surfaces of the water bottle. As a result, individuals can be more susceptible to sickness due to use of a dirty water bottle. Additionally, a reusable water bottle may be disposed of due to its lack of cleanliness, despite otherwise being in condition that would allow for continued use.

SUMMARY OF THE INVENTION

Aspects of the invention provide a solution for disinfecting a surface, such as a mouthpiece located on a top cover of a water bottle, using ultraviolet radiation. A cover assembly can include a cover configured to selectively enclose the surface to be disinfected, such as the mouthpiece. The cover assembly can be configured such that ultraviolet radiation can be emitted into an interior volume at least partially formed by the cover and including the surface. The cover assembly can further include a power source which provides power to one or more ultraviolet light sources that emit the ultraviolet radiation. The cover assembly can be a mouthpiece cover assembly physically separate from a container and the top cover or integrated in the top cover.

Further aspects of the invention provide a container and/or top cover including one or more features for improved cleanliness. The container and/or top cover can include a set of ultraviolet light sources mounted there to, which are configured to emit ultraviolet radiation directed into an interior volume formed by the container and the top cover. The container and/or top cover can further include a power source which provides power to one or more ultraviolet light sources that emit the ultraviolet radiation directed into the interior volume.

Operation of any of the ultraviolet light sources can be managed by a control unit. Such operation can be predetermined and/or determined using input data acquired by one or more sensors. The control unit also can receive data from and/or provide data to a user, e.g., via one or more input/output devices.

A bottom of the container can be selectively removable, which can allow for more ready access to clean the surfaces of the interior volume and/or replace one or more ultraviolet radiation components.

The container can include at least two storage regions, each of which can physically contain a fluid therein. A one way valve can allow fluid to flow only in a direction from one storage region to the other, e.g., in a direction toward the outlet, such as a mouthpiece.

A first aspect of the invention provides a structure comprising: a mouthpiece cover assembly including: a mouthpiece cover; a set of ultraviolet light sources mounted to the mouthpiece cover assembly, wherein the set of ultraviolet light sources are configured to emit ultraviolet radiation directed into an interior volume at least partially formed by the mouthpiece cover; and a power source mounted to the mouthpiece cover assembly, wherein the power source provides power to the set of ultraviolet light sources.

A second aspect of the invention provides a structure comprising: a top cover configured to selectively enclose an opening of a container; a mouthpiece mounted to the top cover; and a mouthpiece cover assembly including: a mouthpiece cover for removably covering the mouthpiece; a set of ultraviolet light sources, wherein the set of ultraviolet light sources are configured to emit ultraviolet radiation directed into an interior volume at least partially formed by the top cover and the mouthpiece cover when the mouthpiece cover is covering the mouthpiece; a control unit configured to manage operation of the set of ultraviolet light sources; and a power source, wherein the power source provides power to the control unit.

A third aspect of the invention provides a water bottle assembly comprising: a container; a top cover configured to selectively enclose an opening of the container; a mouthpiece mounted to the top cover; and a mouthpiece cover assembly including: a mouthpiece cover for removably covering the mouthpiece; a set of ultraviolet light sources, wherein the set of ultraviolet light sources are configured to emit ultraviolet radiation directed into an interior volume at least partially formed by the top cover and the mouthpiece cover when the mouthpiece cover is covering the mouthpiece; a control unit configured to manage operation of the set of ultraviolet light sources; at least one sensor located on at least one of: the top cover or the mouthpiece cover, wherein the at least one sensor is configured to provide data to the control unit indicating a status corresponding to whether the mouthpiece is covered by the mouthpiece cover; and a power source, wherein the power source provides power to the control unit.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

Figure 1A:
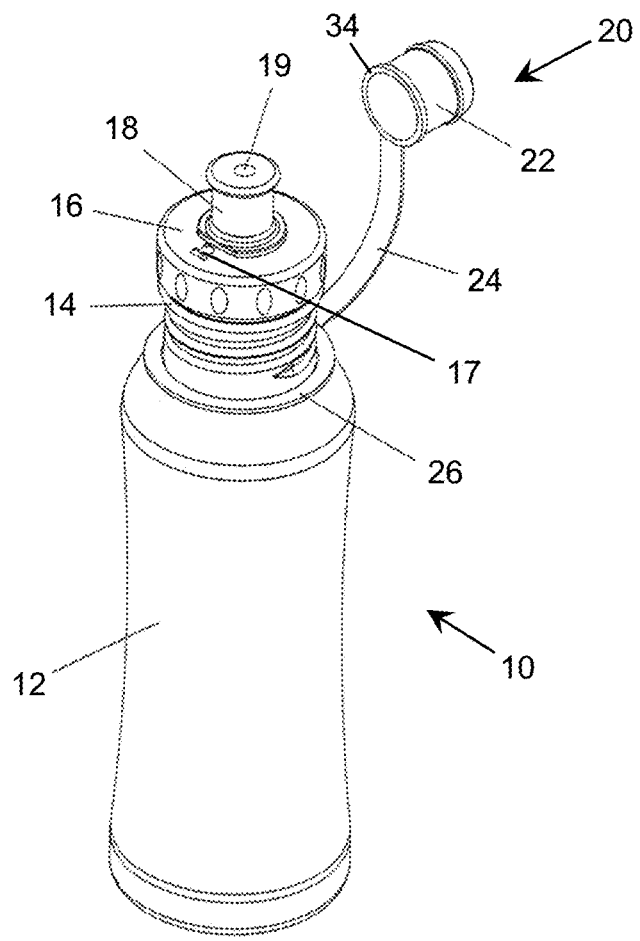
FIG. 1A shows an illustrative water bottle according to an embodiment.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide a solution for disinfecting a surface, such as a mouthpiece of a water bottle, using ultraviolet radiation. A cover assembly can include a cover configured to selectively enclose the surface to be disinfected, such as the mouthpiece. The cover assembly can be configured such that ultraviolet radiation can be emitted into an interior volume at least partially formed by the cover and including the surface. The cover assembly can further include a power source which provides power to one or more ultraviolet light sources that emit the ultraviolet radiation. The cover assembly can be a mouthpiece cover assembly physically separate from a container and top cover or integrated in the top cover. Further aspects provide a container and/or top cover including one or more features for improved cleanliness.

Aspects of the invention provide a solution in which surface(s) are disinfected using ultraviolet radiation. To this extent, the ultraviolet radiation can be directed at the surface(s) in such a manner as to harm (e.g., suppress growth of, reduce an amount of, kill, damage, injure, etc.) any organisms that may be present on the surface(s). The organism(s) can comprise any combination of various types of organisms, such as bacteria, viruses, protozoa, biofilms, mold, and/or the like. The discussion herein refers to the disinfection of one or more surfaces. As used herein, "disinfect" and variants thereof refers to harming one or more target organisms, and include purification, sterilization, and/or the like. Furthermore, as used herein a "disinfected surface" includes a surface that is devoid of any live organisms, a surface that is devoid of any live targeted organisms (but which may include non-targeted organisms), and a surface that includes some live targeted organism(s), but which is substantially free of such organism(s).

As used herein, a layer is a transparent layer when the layer allows at least ten percent of radiation having a target wavelength, which is radiated at a normal incidence to an interface of the layer, to pass there through. Furthermore, as used herein, a layer is a reflective layer when the layer reflects at least ten percent of radiation having a target wavelength, which is radiated at a normal incidence to an interface of the layer. In an embodiment, the target wavelength of the radiation corresponds to a wavelength of radiation emitted or sensed (e.g., peak wavelength+/− five nanometers) by an active region of an optoelectronic device during operation of the device. For a given layer, the wavelength can be measured in a material of consideration and can depend on a refractive index of the material.

An illustrative embodiment of a container described herein is referred to as a water bottle. However, it is understood that aspects of the invention can be directed to any type of container utilized to store any type of fluid. To this extent, aspects of the invention are not limited to water or any type of liquid, but can be applied to any of various types of fluids that may be stored in any of various types of containers. Additionally, while the illustrative embodiment describes disinfection of a mouthpiece, it is understood that a container, and the fluid stored therein, can be utilized for any purpose and human or animal consumption via a mouthpiece is only an illustrative application.

Turning to the drawings, FIG. 1A shows an illustrative water bottle 10 according to an embodiment. In this case, the water bottle 10 comprises a container 12 having a neck 14, and a top cap 16. The top cap 16 can include a mouthpiece 18 with an opening 19 for extraction of a fluid, such as water, stored in the container 12. The opening 19 can be selectively opened and closed, e.g., by lifting and lowering the mouthpiece 18. As seen in FIG. 1A, the top cap 16 can have a maximum diameter that corresponds to the opening at the neck 14 of the container 12. Furthermore, the mouthpiece 18 can have a maximum diameter that is smaller than a maximum diameter of the top cap 16.

In an embodiment, the water bottle 10 can further include a mouthpiece cover assembly 20, which can include a mouthpiece cover 22 configured to selectively cover the mouthpiece 18 and opening 19. As seen in FIG. 1A, the mouthpiece cover 22 can have a maximum diameter that is smaller than the maximum diameter of the top cap 16. Furthermore, in order to cover the mouthpiece 18, the maximum diameter of the mouthpiece cover 22 is larger than the maximum diameter of the mouthpiece 18. In an embodiment, the mouthpiece cover assembly 20 further includes a strap 24 and a securing mechanism 26. The securing mechanism 26 can be secured to the container 12 and/or neck 14 of the water bottle 10 using any solution. For example, as illustrated, the securing mechanism 26 can comprise a ring having an inner diameter sized to fit around the neck 14, but smaller than the maximum diameters of the container 12 and the top cap 16. The strap 24 can be permanently secured to both the mouthpiece cover 22 and the securing mechanism 26 using any solution, such as fabrication as one molded piece. In an embodiment, the mouthpiece cover 22 can be secured by a lock mechanism 17 located on a top surface of the top cap 16 when covering the mouthpiece 12.

Figure 1B:
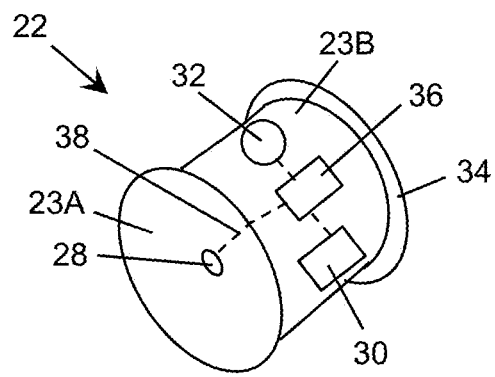
FIG. 1B shows a more detailed schematic view of an illustrative mouthpiece cover according to an embodiment.

In an embodiment, the mouthpiece cover 22 is further configured to disinfect the mouthpiece 18, e.g., from organisms, such as bacteria, that can be transported from a person's mouth, using ultraviolet light. To this extent, as illustrated in FIG. 1B, an embodiment of the mouthpiece cover 22 can include one or more ultraviolet light sources 28. The ultraviolet light source(s) 28 can be positioned and oriented to illuminate at least a portion of the mouthpiece 18 with ultraviolet radiation when the mouthpiece cover 22 is covering the mouthpiece 18.

In the embodiment illustrated in FIG. 1B, one or more ultraviolet light sources 28 can be mounted to a top surface 23A of the mouthpiece cover 22 and can be configured to direct ultraviolet radiation down toward a top surface of the mouthpiece 18 including the opening 19. However, it is understood that this location is only illustrative. To this extent, an embodiment of the mouthpiece cover 22 can include one or more ultraviolet light sources mounted to a side surface 23B of the mouthpiece cover 22. Examples of an ultraviolet light source 28 include, but are not limited to, ultraviolet LEDs, super luminescent LEDs, laser diodes, and/or the like. In one embodiment, the ultraviolet light source 28 can comprise an LED manufactured with one or more layers of materials selected from the group-III nitride material system (e.g., $Al_xIn_yGa_{1-x-y}N$, where $0 \le x$, $y \le 1$, and $x+y \le 1$ and/or alloys thereof).

Any solution for mounting an ultraviolet light source 28 to the mouthpiece 18 can be used. For example, the ultraviolet light source 28 can be embedded within the material of the mouthpiece 18, e.g., with only a light emitting surface exposed. Alternatively, the ultraviolet light source 28 can be adhered to a surface of the mouthpiece 18 using an ultraviolet transparent material, such as a fluoropolymer, polylactide (PLA), sapphire, fused silica, and/or the like.

Additionally, the ultraviolet light source 28 can comprise one or more additional components (e.g., a wave guiding structure, a component for relocating and/or redirecting the ultraviolet light source 28, etc.) to direct and/or deliver the emitted radiation to a particular location/area, in a particular direction, in a particular pattern, and/or the like. Illustrative wave guiding structures include, but are not limited to: a wave guide; a plurality of ultraviolet fibers, each of which terminates at an opening; a diffuser; and/or the like. In an embodiment, the ultraviolet light source 28 can comprise a lens manufactured from an ultraviolet transparent material, which is designed to direct the ultraviolet radiation to one or more locations on the mouthpiece 18. In an embodiment, the mouthpiece cover 22 can comprise a reflective parabolic mirror designed to collimate the ultraviolet radiation emitted by the ultraviolet light source 28. However, it is understood that these components are only illustrative of various possible components. To this extent, it is understood that other optical elements such as prisms, ultraviolet transparent windows, etc., can be employed.

An ultraviolet light source 28 can be configured to emit any type of ultraviolet radiation (e.g., radiation having a peak wavelength in a range of 10 nanometers to 400 nanometers) suitable for performing a desired disinfection of the mouthpiece 18. For example, the ultraviolet light emitted by the ultraviolet light source 28 can have a peak wavelength selected to damage the DNA structure of any bacteria that may be present on the mouthpiece 18. In an embodiment, the ultraviolet light source 28 can emit ultraviolet light in the UV-C wavelength range of approximately 250 nm to approximately 290 nm. In a more particular embodiment, the ultraviolet light has a peak wavelength in a range of 260 nanometers to 285 nanometers.

Additionally, the ultraviolet light source 28 can emit ultraviolet radiation having a peak wavelength in the near-ultraviolet wavelength range of approximately 300 nanometers to 400 nanometers. In a more particular embodiment, the ultraviolet radiation can have a peak wavelength in the UV-A wavelength range of approximately 315 nanometers to 400 nanometers. In another embodiment, the peak wavelength emitted by the ultraviolet light source 28 can be just outside the ultraviolet range, within the highest frequency range of the visible light spectrum, e.g., between 400 nanometers and 420 nanometers. To this extent, a more particular embodiment of an ultraviolet light source 28 can emit radiation having a peak wavelength in a range of 380 nanometers to 420 nanometers. When the mouthpiece cover 22 includes more than one ultraviolet light source 28, the ultraviolet light sources 28 can emit ultraviolet light of distinct peak wavelengths.

In an embodiment, the mouthpiece cover assembly 20 includes all necessary components to enable operation of the ultraviolet light source 28. For example, the mouthpiece assembly 20 can include a power source 30, e.g., mounted to a side surface 23B of the mouthpiece cover 22. The power source 30 can comprise, for example, a battery. In a more particular embodiment, the power source 30 comprises a rechargeable battery. In this case, the mouthpiece cover assembly 20 can include a mechanism for enabling the power source 30 to be recharged, such as a connector for forming an electrical connection with a recharging unit. Alternatively, the power source 30 can be recharged via, for example, one or more solar cells, using a wireless recharging solution, and/or the like.

In an embodiment, a user can selectively turn on and/or off power to the ultraviolet light source 28. To this extent, the mouthpiece cover assembly 20 can include a control mechanism 32, which enables the user to input a request to activate and/or deactivate the ultraviolet light source 28. In an embodiment, the control mechanism 32 comprises a button, which when depressed, activates the ultraviolet light source 28, e.g., for a predetermined fixed amount of time and/or until the control mechanism 32 is depressed again. In an embodiment, the mouthpiece cover assembly 20 includes an indicator as to whether the ultraviolet disinfection is occurring or is not occurring. For example, in an embodiment, the control mechanism 32 can include a visible light that is on while the ultraviolet light source 28 is on and turns off when the ultraviolet light source 28 is off. To this extent, an embodiment of the control mechanism 32 comprises a button with a visible light source.

It is understood that use of a visible light source to indicate an on/off status of the ultraviolet light source 28 is only illustrative of various solutions, visual and non-visual, that can be used to conveying information to a user. To this extent, in other embodiments, a control mechanism can use an audible or visual approach to provide the user with an approximate or exact amount of time remaining for the disinfection process to complete. For example, the control mechanism 32 can comprise multiple visual light sources or a visual light source having an adjustable brightness, which can be altered over time to indicate an approximate amount of time remaining. Similarly, the control mechanism 32 can include a visual (e.g., a countdown timer) or audible indication of time that is conveyed to the user.

However, it is understood that the control mechanism 32, and the operation thereof, is only illustrative. For example, an embodiment can activate the ultraviolet light source 28, e.g., for a predetermined time period, when the mouthpiece cover 22 is secured to the lock mechanism 17 located on the top cap 16. Similarly, an embodiment can prevent activation of the ultraviolet light source 28 via the control mechanism 32 when the mouthpiece cover 22 is not secured to the lock mechanism 17. To this extent, in an embodiment, a rim 34 of the mouthpiece cover 22 can be configured to generate a signal, close a switch, and/or the like, when the rim 34 is secured to the lock mechanism 17. Alternatively, the rim 34 can include one or more sensors, which are configured to generate a signal, close a switch, and/or the like, when a bottom of the rim 34 is in contact with the top surface of the top cap 16. In either case, the rim 34 and/or sensor(s) can comprise a material whose electrical properties change when in contact with a material of the lock mechanism 17 and/or the top cap 16.

In an embodiment, the mouthpiece cover assembly 20 can comprise a control unit 36 (e.g., a microcontroller), which is configured to control operation of the ultraviolet light source 28. Such a control unit 36 can include logic for implementing a more complicated operation regime, e.g., determining a suitable intensity, duration, pattern, location, and/or the like, of the ultraviolet radiation, and operating the ultraviolet light source(s) 28 according to the determined operation regime. The operation can be implemented with input from one or more sensors, such as the rim 34 and/or sensor(s) located thereon, and/or one or more control mechanisms 32, which also can be included in the mouthpiece cover assembly 20 using any solution. Additionally, it is understood that the mouthpiece cover assembly 20 can include various electrical connections 38 between the components included to enable operation of the ultraviolet light source 28.

Furthermore, while the various devices are shown and described as being mounted to the mouthpiece cover 22, it is understood that one or more components can be mounted to a different portion of the mouthpiece cover assembly 20.

For example, the power source 30, control unit 36, and/or control mechanism 32, could be mounted on the strap 24 and/or the securing mechanism 26. In this case, electrical connections 38 between the various components can be routed through (e.g., embedded in) the strap 24 and/or the securing mechanism 26 to the ultraviolet light source 28. Still further, the ultraviolet light source 28 can be mounted on the strap 24 and/or the securing mechanism 26, with a wave guiding structure, such as optical fibers, routed through (e.g., embedded in) the strap 24 and/or the securing mechanism 26 to deliver light generated by the ultraviolet light source 28 to the mouthpiece 18.

An internal surface of the mouthpiece cover 22, an outer surface of the mouthpiece 18, and/or a top surface of the top cap 16 can be configured to contain the ultraviolet radiation within a region defined thereby. In an embodiment, one or more of these surfaces is configured to improve recycling of the ultraviolet radiation within the region. In an embodiment, one or more of such surfaces is capable of reflecting the ultraviolet radiation. In an embodiment, such a reflective surface can comprise polished aluminum, a fluoropolymer, such as ethylene fluorinated ethylene-propylene (EFEP), expanding polytetrafluoroethylene (ePTFE) membrane (e.g., GORE® DRP® Diffuse Reflector Material), polytetrafluoroethylene (PTFE, e.g., Teflon®), and/or the like.

In an embodiment, one or more of the internal surface of the mouthpiece cover 22, the outer surface of the mouthpiece 18, and/or the top surface of the top cap 16 can include a material transparent to the ultraviolet radiation. For example, a transparent layer can be located adjacent to and on a side of a reflective layer of material forming a region in which the ultraviolet light is emitted. In an embodiment, the transparent layer can be configured to provide wave guiding. Such a surface can comprise any suitable ultraviolet transparent material, such as $SiO_2$, $Al_2O_3$, $CaF_2$, $MgF_3$, $HfO_2$, and/or the like. In an embodiment, such a surface can also comprise a fluoropolymer. Regardless, each surface exposed to the ultraviolet radiation generated by the ultraviolet light source 28 can be formed of a material that is suitable for use in conjunction with the ultraviolet radiation, e.g., will not be modified in a potentially hazardous manner. To this extent, when the ultraviolet light source 28 emits UV-C ultraviolet radiation, the internal surface can comprise a material such as stainless steel, quartz window(s), and/or the like, which are capable of withstanding exposure to such radiation.

Figure 2:
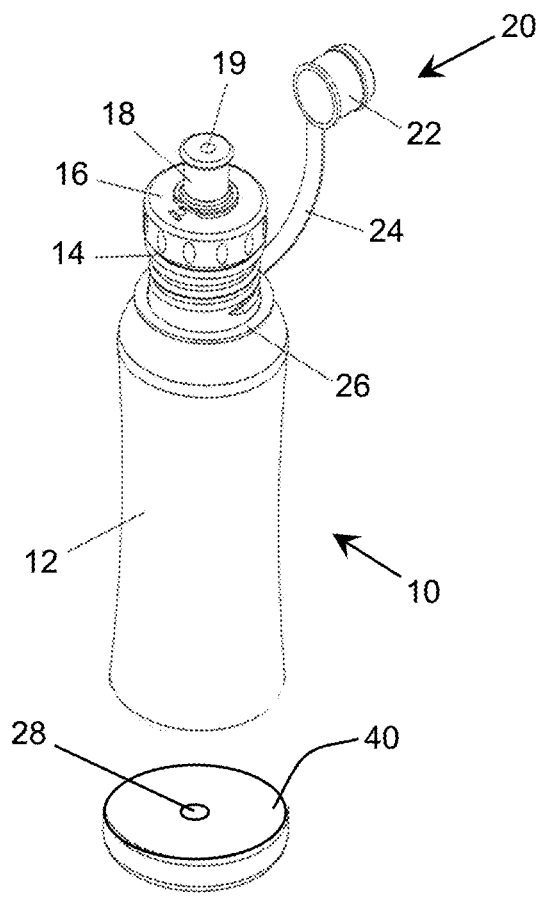
FIG. 2 shows an illustrative water bottle according to another embodiment.

FIG. 2 shows an illustrative water bottle 10 according to another embodiment. In this case, the water bottle 10 can include a mouthpiece cover assembly 20, which can be configured as described in conjunction with FIGS. 1A and 1B. In this embodiment, the water bottle 10 includes a bottom member 40 with an ultraviolet light source 28 located thereon. The ultraviolet light source 28 can be configured to emit ultraviolet light that is directed into an interior of the container 12. The bottom member 40 can comprise a detachable bottom surface for an interior volume formed by the container 12. Alternatively, the container 12 can include a bottom surface through which ultraviolet radiation generated by the ultraviolet light source 28 is directed. The ultraviolet light can be used to, for example, disinfect a fluid, such as water, located within the interior of the container 12 and/or disinfect one or more surfaces defining the interior of the container 12.

While the water bottle 10 is shown including a bottom member 40 with an ultraviolet light source 28, it is understood that the top cap 16 can include one or more ultraviolet light sources 28 configured to emit ultraviolet light directed into the interior of the container 12 and be configured similar to the bottom member 40. Similarly, it is understood that the container 12 can be configured to include one or more ultraviolet light sources 28. For example, a bottom of the container 12 can include an ultraviolet light source 28 without requiring a removable bottom member 40. To this extent, embodiments of a water bottle described herein can be fabricated with any combination of one or more of: a bottom member 40, a mouthpiece cover assembly 20, a container 12, and/or a top cap 16, including one or more ultraviolet light sources 28 and/or one or more components for operating the ultraviolet light source(s) 28 to disinfect one or more surfaces of the water bottle 10 and/or a fluid contained therein. When multiple components of the water bottle 10 include one or more ultraviolet light sources 28, the ultraviolet light sources 28 can be operated autonomously or together. For example, operation of an ultraviolet light source on the mouthpiece cover assembly 20 can be separate from operation of any other ultraviolet light source(s) on the water bottle 10.

Regardless, the ultraviolet light source 28 can be configured similar to the ultraviolet light source described in conjunction with FIGS. 1A and 1B. Additionally, the bottom member 40 can include one or more of the additional components described in conjunction with the mouthpiece cover assembly 20, such as: a power source 30; component(s), such as a control unit 36, wave guiding structures, and/or the like, to direct and/or deliver the emitted radiation to a particular location/area, in a particular direction, in a particular pattern, etc.; a control mechanism 32 for interfacing with a user; etc.

As illustrated, the bottom member 40 can be removable. To this extent, the bottom member 40 can be separately washed and/or enable easier washing of the interior surfaces of the container 12. Alternatively, the container 12 can include a bottom fabricated of a material transparent to ultraviolet radiation. Any of the ultraviolet transparent materials described herein can be used to fabricate a bottom of the container 12. Furthermore, an interior surface of the container 12 and/or an interior surface of the top cap 16 can be formed of a material and/or include one or more structures configured to contain the ultraviolet radiation within the container 12. In an embodiment, one or more of these surfaces is configured to improve recycling of the ultraviolet radiation within the container 12, e.g., by including ultraviolet transparent and/or reflective materials, one or more wave guiding structures, and/or the like.

Additionally, the bottom of the container 12 and the bottom member 40 can be configured to be removably secured to one another. For example, the bottom of the container 12 and the bottom member 40 can include complementary screw threads. Alternatively, a magnetic and/or tension coupling mechanism, and/or the like, can be utilized to removably secure the bottom member 40 to the container 12 in a desired location.

The bottom member 40 can include one or more sensors configured to prevent the ultraviolet light source 28 from emitting ultraviolet light when the bottom member 40 is not secured to the bottom of the container 12. For example, the bottom member 40 can include one or more sensors configured to emit a signal, close a switch, and/or the like, when in contact with the bottom of the container 12. Additionally, the container 12 can include one or more sensors configured to prevent the ultraviolet light source 28 from emitting ultraviolet light when the top cap 16 is not secured to the container 12. For example, the neck 14 of the container 12 can include a sensor which emits a signal, close a switch, and/or the like, when the top cap 16 is attached thereto. While not shown for clarity, it is understood that the container 12 and the bottom member 40 can include the required wiring embedded therein to enable operation of the ultraviolet light source 28.

In an embodiment, a water bottle described herein includes one or more additional light sources and/or sensors. For example, as discussed herein, an embodiment of the water bottle can include one or more visible light sources, e.g., to provide information regarding a status of an ultraviolet disinfection to a user. Additionally, an embodiment of the water bottle can include one or more sensors for determining a level of and/or location of contamination on a surface of the water bottle and/or in the fluid contained therein. For example, an embodiment of a water bottle described herein can include a visible or infrared light source, which can be operated by a microcontroller to induce fluorescent excitation in a contaminant which may be present on the surface, e.g., of the mouthpiece, an interior surface of the container, an interior surface of the top cover, and/or the like. The water bottle can further include a set of sensors configured to sense the fluorescent radiation, which can be correlated with a level of contamination on the corresponding surface. The set of sensors can provide fluorescent radiation data to a control unit, which can process the data to determine whether an ultraviolet treatment of the surface is required and/or modify one or more of an intensity, duration, location, etc., of the ultraviolet radiation in response.

When used to sterilize a fluid contained in the container 12, a set of ultraviolet light sources 28 can emit UV-A and/or visible light in a range between 380-420 nanometers. Such radiation can increase the presence of reactive oxygen species (ROS) within the fluid, which can contribute to the decay of the microorganisms. In an embodiment, an ultraviolet light source 28 that emits UV-A and/or visible radiation can be combined with a photocatalyst to increase hydroxyl group radicals and/or ROS within the fluid to suppress microorganism growth. The photocatalyst can comprise any suitable photocatalyst, such as for example, $TiO_2$, copper, silver, copper/silver particles, platinum/palladium particles, etc., and can be applied to the inner surfaces of the container 14 using any solution. In a more particular embodiment, the inner surfaces of the container 14 can comprise sapphire with platinum/palladium decoration.

To improve disinfection of the fluid, the water bottle 10 can include instructions for the user to shake the water bottle 10 during the disinfection. Additionally, the water bottle 10 can include one or more additional components to improve mixing. For example, a set of mixing elements can be included within the container 12. Furthermore, one or more ultraviolet light sources 28 can be positioned within the fluid, e.g., via structure that extends into the interior of the container 12 and includes an ultraviolet transparent material that encapsulates the ultraviolet light source(s) 28 from the fluid.

Figure 3:
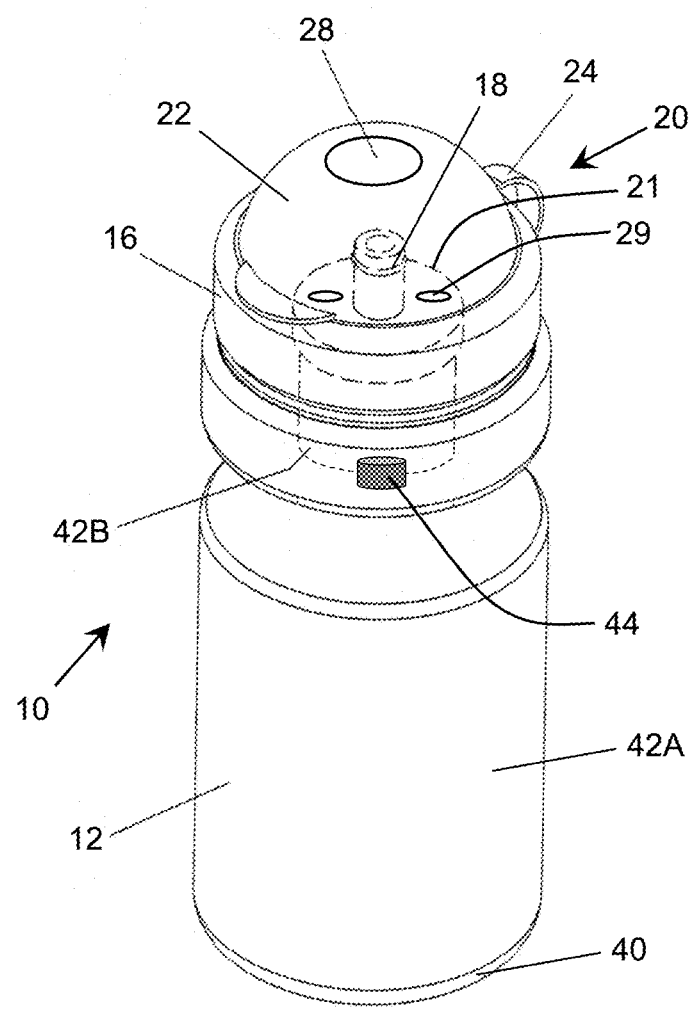
FIG. 3 shows another illustrative water bottle according to an embodiment.

It is understood that embodiments of the mouthpiece cover assembly described herein can have various shapes and/or sizes. For example, FIG. 3 shows another illustrative water bottle 10 according to an embodiment. In this case, the mouthpiece cover assembly 20 includes a larger, semi-spherical mouthpiece cover 22, with an ultraviolet light source 28 located thereon. Such a larger mouthpiece cover 22 can be beneficial for improved disinfection of the mouthpiece 18. While not shown for clarity, it is understood that the mouthpiece cover assembly 20 can include features and/or other components for operating the ultraviolet light source 28 as shown and/or described herein.

In an embodiment, the container 12 can include two storage regions 42A, 42B. The storage regions 42A, 42B can be separated by a structure that restricts the flow of fluid between the storage regions 42A, 42B to one or more one way valves 44. Each one way valve 44 can be configured to allow fluid to flow from the storage region 42A to the storage region 42B, but not the reverse. The storage region 42A can comprise a larger volume than the volume of fluid stored in the storage region 42B, while the storage region 42B can be fluidly connected to the mouthpiece 18. In this case, during use, fluid within the storage region 42B may interact with a user's mouth and, as a result, may be contaminated by the user. However, any such contamination will remain confined to the storage region 42B and the fluid located therein. As a result, the larger volume of fluid stored in the storage region 42A can remain uncontaminated.

To this extent, if desired, the smaller volume of fluid located in the storage region 42B can be discarded without discarding the larger volume of fluid located in the storage region 42A. For example, a user can remove a cover 21 of the storage region 42B and pour out the fluid. In this case, the one way valve 44 can remain closed and only allow fluid to pass there through in response to additional pressure being generated (e.g., by squeezing the container 12). Similarly, the user can disassemble the storage region 42B from the storage region 42A and pour out the fluid before reassembling the regions 42A, 42B. In an embodiment, in addition to restricting the flow of fluid, the one way valve 44 can include a filter, which can be configured to remove large scale particles that may be present in the fluid stored in the region 42A prior to the fluid entering the storage region 42B.

An embodiment of the water bottle 10 can be configured to disinfect the fluid and/or surfaces of the storage region 42B. For example, a capthe cover 21 covering the storage region 42B can include a set of ultraviolet light sources 29. While not shown for clarity, it is understood that the ultraviolet light sources 29 and/or the storage region 42B can include features and/or other components for operating the ultraviolet light sources 29 as shown and/or described herein in order to disinfect the fluid and/or surfaces of the storage region 42B.

An embodiment of the water bottle 10 can include a bottom member 40, which can disinfect a fluid and/or one or more surfaces of the interior of the container 12. In this case, the bottom member 40 can be configured to disinfect the fluid stored within the storage region 42A and/or the interior surfaces of the storage region 42A and can be configured as described herein. In an embodiment, one or both storage regions 42A, 42B contains a photocatalyst, which can improve disinfection as described herein.

In an embodiment, access to the storage region 42A can be obtained via removing the bottom member 40. Alternatively, the container 12 can comprise two distinct portions, one for each storage region 42A, 42B, which can be attached and selectively detached to expose the storage region 42A using any attachment mechanism, e.g., complementary screw threads. However, it is understood that an embodiment of the water bottle 10 can be implemented without the bottom member 40 including an ultraviolet light source. In this case, the fluid placed in the storage region 42A can be known to be safe for consumption.

It is understood that a popup mouthpiece 18 as shown herein is only illustrative of various mouthpiece configurations that can be disinfected using a solution described herein. For other mouthpiece and/or top cover configurations, the placement of the ultraviolet light source(s) can be selected based on the location of the opening 19 and/or orientation of the mouthpiece when placed in a stored configuration to direct the ultraviolet radiation to the desired location(s).

Figure 4:
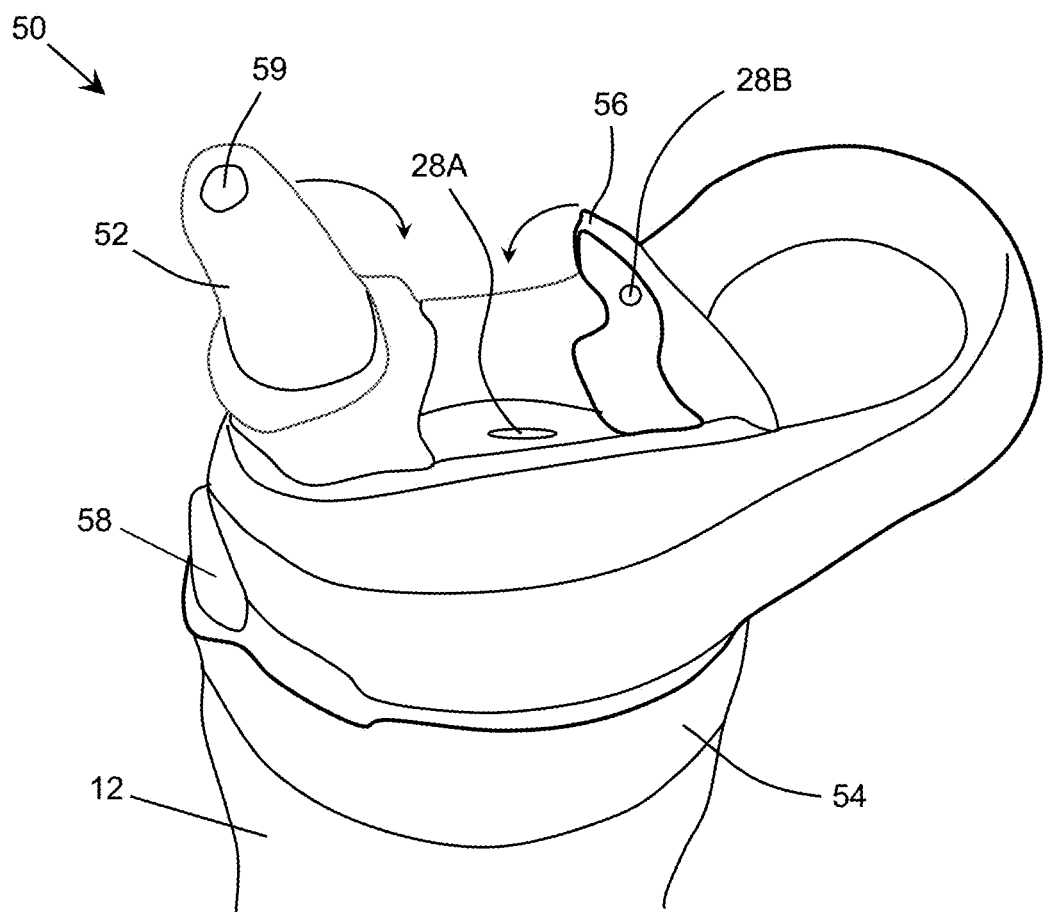
FIG. 4 shows an illustrative top cover with a retractable mouthpiece according to an embodiment.

To this extent, FIG. 4 shows an illustrative top cover 50 with a retractable mouthpiece 52 (e.g., a retractable wide straw) according to an embodiment. In this case, the top cover 50 includes a top cap 54, which can be removably attached to a top of a container 12 of a water bottle using any solution, e.g., complementary screw threads. The top cover 50 further includes an integrated mouthpiece cover assembly, which includes a rotatable mouthpiece cover 56. To retract the mouthpiece 52 when not in use, the user can first rotate the mouthpiece 52 in the direction shown and then rotate the mouthpiece cover 56 in the direction shown. Once fully lowered, the mouthpiece cover 56 can be held in place by a latch mechanism (not shown). To open the retractable mouthpiece 52 for use, the user can depress a button 58, which causes the latch mechanism to release and the mouthpiece cover 56 and retractable mouthpiece 52 to rotate to their illustrated positions (e.g., via spring mechanisms).

The top cover 50 further includes a set of ultraviolet light sources 28A, 28B, which are configured to irradiate the retracted mouthpiece 52 to disinfect the mouthpiece 52. To this extent, the top cover 50 can include various other features and/or other components for operating the ultraviolet light sources 28A, 28B as shown and/or described herein in order to disinfect the mouthpiece 52. To this extent, the top cover 50 can include a control unit that operates the ultraviolet light sources 28A, 28B when the mouthpiece 52 is retracted and secured by the mouthpiece cover 56. In an embodiment, the control unit can receive an indication that the mouthpiece cover 56 is secured from one or more sensors, e.g., associated with the latch mechanism. In this case, in response to the latch mechanism being released, e.g., by depression of the button 58, the control unit can turn off the ultraviolet light sources 28A, 28B, if necessary. In an embodiment, the button 58 includes a visible indicator indicating that an ultraviolet treatment is being performed on the mouthpiece 52.

The mouthpiece 52, mouthpiece cover 56 and top surface of the top cap 54 can form an enclosure within which the ultraviolet radiation emitted by the ultraviolet light sources 28A, 28B is shone. Each of these components can be fabricated of a suitable material, which can facilitate containment and/or recycling of the ultraviolet light therein. In an embodiment, the mouthpiece 52 is fabricated of an ultraviolet transparent material, which allows ultraviolet light to penetrate the outer walls of the mouthpiece 52 to disinfect an interior region defined by the opening 59. Furthermore, one or more ultraviolet light sources can be located to direct ultraviolet radiation directly into the opening 59.

It is understood that embodiments described herein can be specifically tailored to provide a container (e.g., water bottle) designed to be safer for drink sharing, such as may be used by athletic teams or other groups of individuals. As described herein, an embodiment can comprise a control unit that can turn on the disinfection process, e.g., after each use of the water bottle. The control unit can determine use of the water bottle using data from any of various possible sensors. For example, the use can be determined by sensing an opening of a cover for the mouthpiece, a change in bottle orientation, or other indicators of use, such as changes in a weight of the fluid stored within the water bottle. In addition, the control unit can adjust the radiation intensity and/or duration based on one or more of: the amount of water in the bottle, the frequency of the use of the water bottle, data collected by fluorescent sensors, and/or the like.

As used herein, unless otherwise noted, the term "set" means one or more (i.e., at least one) and the phrase "any solution" means any now known or later developed solution. The singular forms "a," "an," and "the" include the plural forms as well, unless the context clearly indicates otherwise. Additionally, the terms "comprises," "includes," "has," and related forms of each, when used in this specification, specify the presence of stated features, but do not preclude the presence or addition of one or more other features and/or groups thereof. It is understood that, unless otherwise specified, each value is approximate and each range of values included herein is inclusive of the end values defining the range. As used herein, unless otherwise noted, the term "approximately" means a reasonable amount of deviation of the modified term such that the end result is not meaningfully changed. In an embodiment, approximately is inclusive of values within +/− ten percent of the stated value when this deviation does not result in a meaningful change to the modified value, term, range, etc.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A structure comprising:
   a container, the container having an opening to receive a fluid, wherein the container includes:
      a first fluid storage region;
      a second fluid storage region in fluid communication with a mouthpiece, wherein the second fluid storage region is selectively enclosed by a top cover; and
      a one way valve allowing fluid to flow only in a direction from the first fluid storage region to the second fluid storage region, wherein the one way valve comprises a filter to filter particles from the fluid to the first fluid storage region before entering the second fluid storage region;
   a removable top cap configured to be selectively secured to the container near the opening of the container, the mouthpiece having a maximum diameter that is smaller than the maximum diameter of the top cap;
   a set of top cover ultraviolet radiation light sources mounted to the top cover over the second fluid storage region and configured to emit ultraviolet radiation directed into an interior volume of the second fluid storage region; and
   a mouthpiece cover assembly configured to be removably attached to at least one of: the container or the top cap, the mouthpiece cover assembly including:
      a mouthpiece cover having a maximum diameter that is larger than the maximum diameter of the mouthpiece, wherein the mouthpiece cover is configured to fit over the mouthpiece, enclosing the mouthpiece without contacting the mouthpiece and without enclosing a top surface of the top cap, wherein the mouthpiece cover contacts the top surface of the top cap when enclosing the mouthpiece;
      a set of ultraviolet light sources, wherein at least one ultraviolet light source is mounted to the mouthpiece cover, wherein the set of ultraviolet light sources are configured to emit ultraviolet radiation directed into an interior volume at least partially formed by the mouthpiece cover and an interior volume formed by the container and the top cap surrounding the mouthpiece; and a power source mounted to the mouthpiece cover, wherein the power source provides power to the set of ultraviolet light sources.

2. The structure of claim 1, wherein the mouthpiece cover assembly further includes a control unit configured to manage operation of the set of ultraviolet light sources.

3. The structure of claim 2, further comprising:
at least one sensor located on at least one of: the top cap of the container or the mouthpiece cover of the mouthpiece cover assembly, wherein the at least one sensor is configured to provide data to the control unit indicating a status corresponding to whether the mouthpiece of the container is covered by the mouthpiece cover.

4. The structure of claim 3, wherein the control unit is configured to automatically turn on the set of ultraviolet light sources in response to the mouthpiece being covered by the mouthpiece cover.

5. The structure of claim 1, wherein the mouthpiece cover assembly further includes a visual indicator configured to indicate that at least one of the set of ultraviolet light sources is on.

6. The structure of claim 1, wherein at least one interior surface of the mouthpiece cover includes an ultraviolet reflective material.

7. The structure of claim 1, wherein the mouthpiece cover assembly further includes a securing mechanism for securing the mouthpiece cover to at least one of: the container or the top cap of the container.

8. The structure of claim 1, wherein at least one of the container or the top cap of the container includes:
an additional set of ultraviolet light sources mounted to the at least one of the container or the top cap, wherein the additional set of ultraviolet light sources are configured to emit ultraviolet radiation directed into the interior volume formed by the container and the top cap; and
an additional power source mounted to the at least one of the container or the top cap, wherein the additional power source provides power to the additional set of ultraviolet light sources.

9. The structure of claim 1, wherein a bottom of the container is removable to provide access to the interior volume formed by the container and the top cap, and wherein the bottom of the container comprises at least one ultraviolet light source configured to irradiate the interior volume formed by the container and the top cap.

10. The structure of claim 1, wherein the cover further includes:
a cover power source configured to provide power to the set of cover ultraviolet light sources.

11. A bottle assembly, comprising:
a container having an opening defining an internal volume for storing fluid, wherein the internal volume of the container includes a first fluid storage region, a second fluid storage region, and a one way valve allowing fluid to flow only in a direction from the first fluid storage region to the second fluid storage region, wherein the one way valve includes a filter to filter particles from the fluid in the first fluid storage region before entering the second fluid storage region;
a top cap configured to be selectively secured to the container near the opening of the container;
a top cover configured to selectively enclose the second fluid storage region of the container, wherein the top cover is configured to selectively enclose the opening of the container;
a mouthpiece mounted to the top cover, wherein the mouthpiece is in fluid communication with the second fluid storage region; and
a mouthpiece cover assembly configured to selectively enclose the top cover and the mouthpiece, the mouthpiece cover assembly including:
a mouthpiece cover for covering the top cover and the mouthpiece, wherein the mouthpiece cover is configured to cover the top cover and the mouthpiece without contacting a surface of the top cover or a surface of the mouthpiece, wherein the mouthpiece cover and the top cap at least partially form an interior cap volume when the mouthpiece cover contacts a top surface of the top cap;
at least one ultraviolet light source mounted to a top surface of the mouthpiece cover, wherein the at least one ultraviolet light source is configured to emit ultraviolet radiation directed into the interior cap volume toward the mouthpiece;
a set of ultraviolet light sources mounted to the top cover over the second fluid storage region, wherein the set of ultraviolet light sources are configured to emit ultraviolet radiation directed into the second fluid storage region;
a control unit configured to manage operation of the at least one ultraviolet light source and the set of ultraviolet light sources; and
a power source, wherein the power source provides power to the control unit, the at least one ultraviolet light source, and the set of ultraviolet light sources.

12. The bottle assembly of claim 11, wherein the mouthpiece cover assembly is integrated into the top cap.

13. The bottle assembly of claim 11, wherein a bottom of the container is removable, and wherein the bottom of the container comprises at least one ultraviolet light source configured to irradiate the internal volume of the container including the first fluid storage region.

14. The bottle assembly of claim 11, wherein the mouthpiece cover assembly further comprises a securing mechanism for securing the mouthpiece cover to at least one of: the container or the top cap of the container.

15. The bottle assembly of claim 11, further comprising at least one sensor located on at least one of: the top cap of the container or the mouthpiece cover of the mouthpiece cover assembly, wherein the at least one sensor is configured to provide data to the control unit indicating a status corresponding to whether the mouthpiece of the container is covered by the mouthpiece cover.

16. A water bottle assembly comprising:
a container having an internal volume for storing fluid, wherein the internal volume of the container includes a first fluid storage region, a second fluid storage region, a one way valve allowing fluid to flow only in a direction from the first fluid storage region to the second fluid storage region, and a removable bottom portion that provides access to the first fluid storage region;
a top cap configured to be secured to the container opposite the removable bottom portion;
a top cover configured to selectively enclose the second fluid storage region of the container at a location near the top cap;

a mouthpiece mounted to the top cover, wherein the mouthpiece is in fluid communication with the second fluid storage region; and a mouthpiece cover assembly configured to selectively enclose the top cover and the mouthpiece, the mouthpiece cover assembly including:

a mouthpiece cover for covering the top cover and the mouthpiece, wherein the mouthpiece cover is configured to cover the top cover and the mouthpiece without contacting a surface of the top cover or a surface of the mouthpiece, wherein the mouthpiece cover and the top cap at least partially form an interior cap volume when the mouthpiece cover contacts a top surface of the top cap;

at least one ultraviolet light source mounted to a top surface of the mouthpiece cover, wherein the at least one ultraviolet light source is configured to emit ultraviolet radiation directed into the interior cap volume toward the mouthpiece;

a set of ultraviolet light sources mounted to the top cover over the second fluid storage region, wherein the set of ultraviolet light sources are configured to emit ultraviolet radiation directed into the second fluid storage region;

a control unit configured to manage operation of the at least one ultraviolet light source and the set of ultraviolet light sources;

at least one sensor located on at least one of: the top cap or the mouthpiece cover, wherein a first sensor is configured to provide data to the control unit indicating a status corresponding to whether the mouthpiece is covered by the mouthpiece cover; and a power source, wherein the power source provides power to the control unit, the at least one ultraviolet light source, and the set of ultraviolet light sources.

17. The water bottle assembly of claim 16, wherein the mouthpiece cover assembly further includes a control mechanism, wherein the control mechanism enables a user to interface with the control unit.

18. The water bottle assembly of claim 16, further comprising at least one visible light source to induce fluorescent excitation in a contaminant present on a surface or in at least one of the internal volume of the container, the top cap, the mouthpiece, or the interior volume formed by the top cap and the mouthpiece cover.

19. The water bottle assembly of claim 18, wherein a second sensor is configured to sense fluorescent radiation associated with the fluorescent excitation, wherein the control unit is configured receive fluorescent radiation data from the second sensor and determine whether an ultraviolet treatment is required of the area which corresponds to the received fluorescent radiation data, and/or modify one or more of an intensity, duration, and location of the ultraviolet radiation emitted from at least one of the at least one ultraviolet light source or the set of ultraviolet light sources in response to the determination of the fluorescent radiation data.

20. The water bottle assembly of claim 16, wherein the bottom portion of the container comprises at least one ultraviolet light source configured to irradiate the internal volume of the container including the first storage region.

* * * * *